(12) United States Patent
Mathur et al.

(10) Patent No.: US 7,839,282 B1
(45) Date of Patent: Nov. 23, 2010

(54) CAPACITANCE PROBE FOR DETECTION OF ANOMALIES IN NON-METALLIC PLASTIC PIPE

(75) Inventors: Mahendra P. Mathur, Pittsburgh, PA (US); James L. Spenik, Morgantown, WV (US); Christopher M. Condon, Morgantown, WV (US); Rodney Anderson, Grafton, WV (US); Daniel J. Driscoll, Morgantown, WV (US); William L. Fincham, Jr., Fairmont, WV (US); Esmail R. Monazam, Morgantown, WV (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 12/844,986

(22) Filed: Jul. 28, 2010

Related U.S. Application Data

(63) Continuation-in-part of application No. 11/964,505, filed on Dec. 26, 2007.

(60) Provisional application No. 60/882,027, filed on Dec. 27, 2006.

(51) Int. Cl.
*G08B 13/26* (2006.01)
*G08B 21/00* (2006.01)
*G01R 31/08* (2006.01)
*G01R 27/26* (2006.01)

(52) U.S. Cl. ............... 340/562; 340/561; 340/657; 324/519; 324/686; 324/687; 324/688

(58) Field of Classification Search ......... 340/561–562, 340/657; 324/519, 686, 688
See application file for complete search history.

(56) References Cited

U.S. PATENT DOCUMENTS

| | | | | |
|---|---|---|---|---|
| 4,481,816 A * | 11/1984 | Prentice | .............. | 73/865.8 |
| 4,581,938 A * | 4/1986 | Wentzell | .............. | 73/623 |
| 4,852,391 A * | 8/1989 | Ruch et al. | .............. | 73/40.5 R |
| 4,986,314 A * | 1/1991 | Himmler | .............. | 138/97 |
| 5,864,229 A * | 1/1999 | Lund | .............. | 324/240 |
| 6,249,130 B1 * | 6/2001 | Greer | .............. | 324/687 |
| 6,427,602 B1 * | 8/2002 | Hovis et al. | .............. | 104/138.1 |
| 6,781,387 B2 * | 8/2004 | Goldfine et al. | .............. | 324/658 |
| 7,414,395 B2 * | 8/2008 | Gao et al. | .............. | 324/220 |
| 2005/0030724 A1 * | 2/2005 | Ryhanen et al. | .............. | 361/760 |
| 2005/0040832 A1 * | 2/2005 | Steele et al. | .............. | 324/640 |
| 2005/0069178 A1 * | 3/2005 | Nysaether et al. | .............. | 382/124 |
| 2005/0104600 A1 * | 5/2005 | Cotton | .............. | 324/519 |
| 2005/0253597 A1 * | 11/2005 | Miller | .............. | 324/662 |

* cited by examiner

*Primary Examiner*—Benjamin C Lee
*Assistant Examiner*—Andrew Bee
(74) *Attorney, Agent, or Firm*—James B. Potts; Mark P. Dvorscak

(57) ABSTRACT

The disclosure relates to analysis of materials using a capacitive sensor to detect anomalies through comparison of measured capacitances. The capacitive sensor is used in conjunction with a capacitance measurement device, a location device, and a processor in order to generate a capacitance versus location output which may be inspected for the detection and localization of anomalies within the material under test. The components may be carried as payload on an inspection vehicle which may traverse through a pipe interior, allowing evaluation of nonmetallic or plastic pipes when the piping exterior is not accessible. In an embodiment, supporting components are solid-state devices powered by a low voltage on-board power supply, providing for use in environments where voltage levels may be restricted.

20 Claims, 8 Drawing Sheets

CAPACITANCE PROBE FOR DETECTION OF ANOMALIES IN NON-METALLIC PLASTIC PIPE

RELATION TO OTHER APPLICATIONS

This patent application is a continuation in part of and claims priority from provisional patent application 60/882,027, filed Dec. 27, 2006, and non-provisional patent application Ser. No. 11/964,505 filed Dec. 26, 2007, which are hereby incorporated by reference.

GOVERNMENT INTERESTS

The United States Government has rights in this invention pursuant to the employer-employee relationship of the Government to the inventors as U.S. Department of Energy employees and site-support contractors at the National Energy Technology Laboratory.

FIELD OF THE INVENTION

The disclosure relates to analysis of materials and specifically to the nondestructive testing of materials by electronic means.

BACKGROUND

Since the 1970's a large portion of gas distribution lines have been fabricated from polyethylene (PE). Also, as of 1995, about one-third of the 1.5 million miles of gas distribution pipelines in this country was made from PE. A special investigative report issued by the NTSB indicates that hundreds of thousands of miles of plastic pipe installed from the 1960's through the early 1980's may be vulnerable to a phenomenon called "brittle-like cracking". Brittle-like failures, as a national average, may represent the second most frequent failure mode for older plastic piping, exceeded only by excavation damage.

Brittle-like cracking is characterized by the appearance of cracks through the wall of pipe with no visible deformations. This type of failure was not considered during testing in the early years of plastic pipe use; Only hoop stress was considered. When hoop stress was applied to pipe during laboratory testing the usual failure mode was a ductile fracture characterized by significant deformation. The long term hydrostatic strength of polyethylene pipe used for natural gas service was determined by subjecting pipe samples to various hoop stresses and noting the time to failure. A log-log plot of time vs hoop stress was created and then extrapolated to 100,000 hours.

The hoop stress at this point represented the hydrodynamic strength. Only internal pressures were used as design criteria for plastic pipe, external loadings that could cause additional stresses were not considered. It was believed that these stresses would be relieved by local yielding because of the expected ductile behavior of the plastic pipes. After the middle of the 1980's standards were changed and the phenomenon of brittle-like cracking was accounted for. Polyethylene pipe used in new services probably will not exhibit brittle-like cracking but hundreds of thousands of miles of existing pipe may.

A number of techniques exist in literature to determine the integrity of metallic pipelines for gas distribution and gas transmission, such as ultrasonic, eddy current and acoustic wave to name a few. However, no satisfactory technique exists in literature that determines the flaws and defects in non-metallic or plastic pipeline. In particular, no satisfactory techniques exists for the inspection of non-metallic or plastic pipeline in-situ, when significant access constraints and inspection environment concerns may significant logistical hurdles.

To overcome these problems, a suitable sensing device must be able to reliably and dependably detect flaws or abnormalities in plastic and non-metallic pipe.

Herein, we describe a device and method based on capacitance measurements that can detect flaws in already buried plastic gas distribution pipelines. A probe has been designed that can be inserted into the natural gas pipelines to examine the spatial dielectric characteristics of the pipe walls. The probe employs a sensor that measures the capacitance (or permittivity) of the pipeline wall. Defects are indicated by variations in the permittivity of the non-metallic or plastic material.

SUMMARY

The apparatus disclosed includes a capacitive sensor comprised of a driven electrode, a guard electrode, and a ground electrode. The capacitive sensor is arranged such that an electric field extends from the driven electrode to the ground electrode when a voltage is applied across the electrodes. The guard electrode is juxtaposed between the driven electrode and the ground electrode. The capacitive sensor is placed in close proximity to a non-metallic or plastic dielectric material such as a piping wall, and the capacitance of the dielectric material is monitored within an area and compared to the capacitance of the dielectric in surrounding areas. Anomalies in the capacitance indicate anomalies in the dielectric material. The capacitive sensor is constructed such that the driven electrode, the guard electrode, and the ground electrode are located on the same side of the dielectric material, so that an applied voltage creates a fringing field and measurements can be made with access to only the inside surface of a non-metallic or plastic pipeline.

The apparatus further includes a capacitance measurement device, power supply, a location device, and a processor. The processor is in data communication with the capacitance measurement device. The processor receives and correlates capacitance and location data and may provide a direct reading correlation or record the correlation for later viewing.

In operation, the capacitive sensor is placed in close proximity to a dielectric material such as a non-metallic or plastic pipe wall, and the capacitance measurement device energizes the driven electrode and the guard electrode, such that a fringing electric field extends between the driven electrode and the ground electrode through a measuring volume of the dielectric material. The capacitance measurement device determines a capacitance between the driven electrode and the ground electrode based on an evaluation of the RC time constant in the RC circuit formed by the capacitance measurement device, the driven electrode, and the ground electrode. The processor receives and correlates the capacitance signal and the location signal. The capacitance sensor is positioned at a second location and a second capacitance measurement and location are correlated. The process may be repeated for any number of measurement points. Anomalies in the capacitance measurement as compared to the capacitances indicated in neighboring areas indicates an anomaly in the dielectric material at the measurement location.

In an embodiment, the capacitive sensor, the power supply, the location measurement device, and the processor are mounted on an inspection vehicle designed to travel through the interior of a piping length, so that inspection may be conducted on piping sections where the outside of the pipe is inaccessible. The processor may monitor the location signal from the location device as the inspection vehicle traverses the piping length, and receive a capacitance signal from the capacitance measurement device when a predetermined displacement has occurred since the previous measurement point. In an embodiment, a plurality of capacitive sensors may be mounted on the inspection vehicle so that a greater circumferential percentage of the piping length may be inspected with a single pass of the inspection vehicle. The processor may provide direct reading of capacitance and location, or may store the correlations for observation following the pass of the inspection vehicle through the piping length.

In an embodiment, the capacitance measurement device, the processor, and the location device may be comprised of solid-state devices receiving power from an on-board battery, such as a 9 volt alkaline or nickel metal hydride battery. Determination of capacitance based on RC time constant evaluation using integrated components allows operation at reduced voltage levels.

The novel apparatus and principles of operation are further discussed in the following description

DETAILED DESCRIPTION

Figure 1:
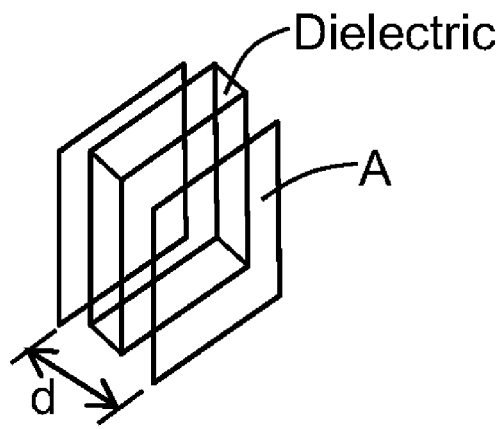
FIG. 1 illustrates a parallel plate capacitor.

The following description is provided to enable any person skilled in the art to use the invention and sets forth the best mode contemplated by the inventor for carrying out the invention. Various modifications, however, will remain readily apparent to those skilled in the art, since the principles of the present invention are defined herein specifically to provide an apparatus and method for the detection of anomalies in non-metallic and plastic pipelines.

The apparatus disclosed includes a capacitive sensor comprised of a driven electrode, a guard electrode, and a ground electrode, arranged such that an electric field extends from the driven electrode to the ground electrode when a voltage is applied across the electrodes. The guard electrode is juxtaposed between the driven electrode and the ground electrode. The capacitive sensor is placed in close proximity to a nonmetallic or plastic dielectric material such as a piping wall, and the capacitance of the dielectric material is monitored within a measuring volume and compared to the capacitance of the dielectric in surrounding volumes. Anomalies in the capacitance indicate anomalies in the dielectric material. The capacitive sensor is constructed such that the driven electrode, the guard electrode, and the ground electrode are located on the same side of the dielectric material, so that an applied voltage creates a fringing field and measurements can be made with access to only the inside surface of a non-metallic or plastic pipeline.

The apparatus further includes a capacitance measurement device electrically connected to the driven electrode and the ground electrode. The capacitance measurement device forms an RC circuit having an RC time constant with the driven electrode and the ground electrode, and determines a capacitance between the driven electrode and the ground electrode based on evaluation of the RC time constant. The capacitance measurement device is further electrically connected to a shield driver, which supplies a voltage to the guard electrode that mimics the voltage of the driven electrode. The shield driver may be a component separate from the capacitance measurement device, or may be an inherent feature built-in to the capacitance measurement device. Further, the capacitance measurement device is capable of providing a capacitance signal, where the capacitance signal is representative of the capacitance determined through evaluation of the RC time constant. The apparatus further includes a power supply electrically connected to the capacitance measurement device. In an embodiment, the capacitance measurement device is a capacitance-to-digital converter and the power supply is a nickel metal hydride battery.

The apparatus further includes a location measurement device for determining the location of the capacitive sensor with respect to a fixed point of reference. The location measurement device is maintained at a fixed position relative to the capacitive sensor, so that sensed movement of the location measurement device reflects corresponding movement of the capacitive sensor. Further, the location measurement device is capable of providing a location signal. In an embodiment, the location measurement device is an optical mouse encoder.

The apparatus further includes a processor in data communication with at least the capacitance measurement device and the location measurement device. The processor correlates the capacitance signal and the location signal, and may provide a direct reading correlation or record the correlation for later viewing. In an embodiment, the processor is a microcontroller having an integrated circuit programmed to receive and correlate the capacitance signal and the location signal. In an embodiment, the processor accumulates received location data and directs the capacitance measurement device to determine a capacitance based on predetermined location data values.

In operation, the capacitive sensor is placed in close proximity to a dielectric material such as a non-metallic or plastic pipe wall with the driven electrode, the guard electrode, and the ground electrode at a ground voltage, and the capacitance measurement device energizes the driven electrode and guard electrode, establishing a fringing electric field which at least partially extends through a measuring volume of the dielectric material. The capacitance measurement device determines a capacitance between the driven electrode and the ground electrode based on an evaluation of the RC time constant in the circuit formed by the capacitance measurement device, the driven electrode, and the ground electrode. The location measurement device determines the location of the capacitive sensor with respect to a fixed point of reference. The processor receives and correlates the capacitance signal and the location signal. The capacitance sensor is positioned at a second location and a second capacitance measurement and location are correlated. The process may be repeated for any number of measurement points. Anomalies in the capacitance measured as compared to the capacitances indicated in neighboring areas indicates an anomaly in the dielectric material at the measurement location.

In an embodiment, the capacitive sensor, the power supply, the location measurement device, and the processor are mounted on an inspection vehicle designed to travel through the interior of a piping length, so that inspection may be conducted on piping sections where the outside of the pipe is inaccessible. The inspection vehicle may traverse the piping length such that the capacitive sensor takes a plurality of capacitive measurements on the inner piping surface. The processor may monitor the location signal from the location device and receive a capacitance signal from the capacitance measurement device when the location signals received indicate a predetermined displacement has occurred since the previous measurement point. The processor correlates the capacitance measurement with the location signal, so that comparison of the measured capacitance with the surrounding material may be conducted. In an embodiment, a plurality of capacitive sensors may be mounted on the inspection vehicle so that each capacitive sensor determines a capacitance at a separate circumferential location inside the piping when the inspection vehicle achieves a given location, so that inspection of the piping length along multiple lines substantially parallel to the axial dimension may be conducted with a single pass of the inspection vehicle through the piping length. The processor may provide direct reading of capacitance and location, or may store the correlations for observation following the pass of the inspection vehicle through the piping length.

Principles of Operation

Capacitance is the ability of a body to hold an electrical charge. As shown in FIG. 1, the capacitance (C) between two plates is a ratio between charge (Q) accumulated on the plates and the associated potential drop (V). If the distance between the plates of a parallel plate capacitor is d, the electric field intensity (E) is given by the ratio V/d and by Gauss' law $E=Q/A\in$, where A is the area of overlap of the two plates and e is the permittivity of the material between the plates. As is known in the art, for a parallel plate capacitor such that shown at FIG. 1, capacitance is directly proportional to the surface area A of the conductor plates and inversely proportional to the separation distance between the plates. If the charges on the plates are +Q and −Q and fringing field effects are ignored, then the capacitance C is given by $C=Q/V=(kA\in_0)/d$, where k is the dielectric constant of the material between the plates and $\in_0$ is the permittivity of free space.

When a capacitor with a dielectric material between the plates such as that shown at FIG. 1 is in a circuit with a resistivity R and a DC source of voltage $V_0$, and the capacitor is initially uncharged, when the voltage $V_0$ is applied to the circuit a time dependent voltage v(t) across the capacitor may be determined by $v(t)=V_0(1-e^{-t/RC})$, as is known in the art. Knowledge of v(t) at a time t and knowledge of circuit resistivity R allows determination of the capacitance C. Further, if comparison of the capacitance of two different dielectric materials between the plates is desired, then simple comparison of the v(t) at the time t after the voltage $V_0$ is applied could be sufficient to indicate a similarity or dissimilarity between the two dielectric materials in terms of their respective capacitances.

Figure 2:
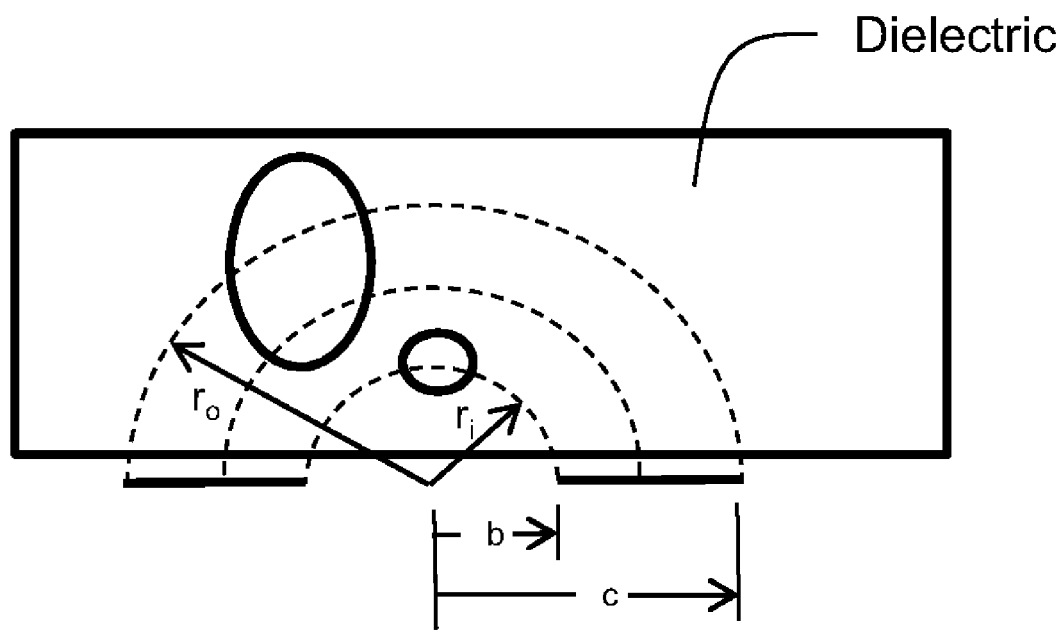
FIG. 2 illustrates a parallel plate capacitor.

When the plates are arranged in a coplanar arrangement, such as is shown in FIG. 2, the electric field extends from one plate, through the material in question, to the other plate. This changes the operation of the capacitor into one with only a fringing field. For equal sized electrodes the electric field follows a circular arc, and the minimum penetration distance of the electric field $r_i$ is equal to half the distance between the inner edges of the two electrodes, indicated as b. The maximum penetration $r_o$ is half the distance between the outer edges of the electrodes, indicated as c. This arrangement is used in common products such as "stud finders" but is inadequate for detection of defects within the walls of plastic pipes. Stray capacitances caused by wires in the electric circuit and other nearby conductive surfaces contribute noise above the required precision to detect abnormalities in a plastic pipe.

Figure 3:
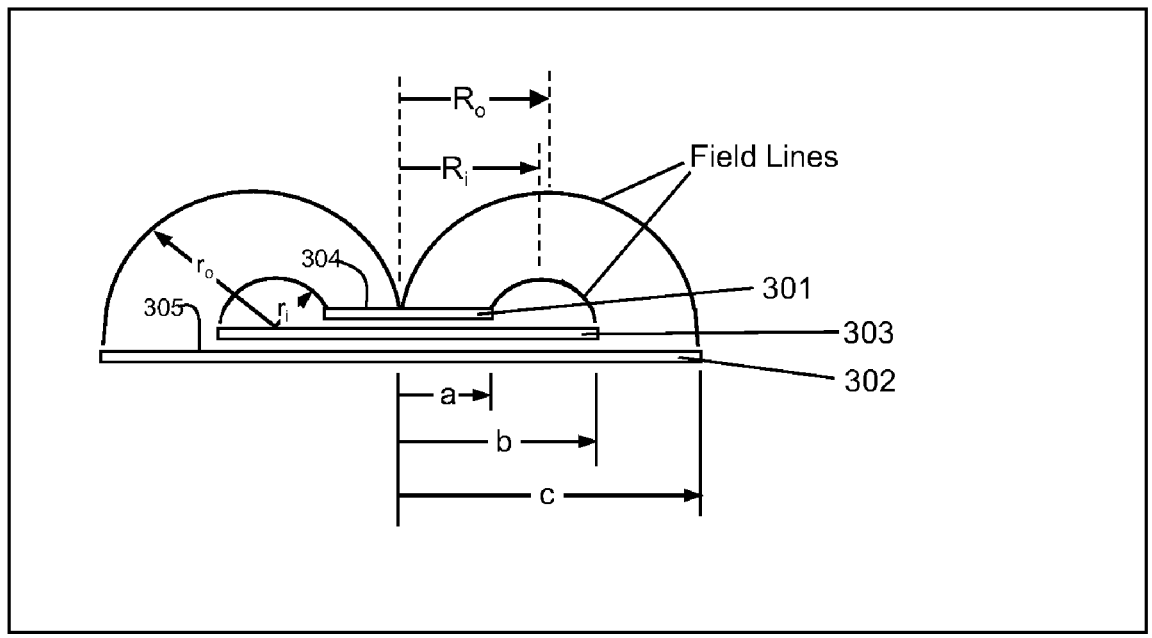
FIG. 3 illustrates a diagram of a probe head configuration.

The problem of stray capacitance may be mitigated with a guard electrode. FIG. 3 illustrates a capacitive sensor comprised of driven electrode 301, ground electrode 302, and guard electrode 303. In the embodiment illustrated driven electrode 301 is a disc of radius a, ground electrode 302 is a disc of radius c, and guard electrode 303 is a disc of radius b. The guard electrode 303 is placed between the driven electrode 301 and the ground electrode 302. The guard electrode 303 is driven by a separate circuit (not shown) which mimics the voltage of the driven electrode 301. Non-electrically conducting insulating layers may be placed between each electrode. The guard electrode 303 is equal to or larger in diameter than the driven electrode 301, and acts to shield driven electrode 301 from stray capacitances.

When driven electrode 301 and guard electrode 303 are energized with a voltage signal, a fringing electric field exists between driven electrode 301 and ground electrode 302. The fringing electric field is maximized by guard electrode 303, which by mimicking the voltage signal applied to driven electrode 301, mitigates the non-fringing field which would otherwise result between driven electrode 301 and ground electrode 303.

In the embodiment shown at FIG. 3, the penetration depth of the probe can be calculated by examining the path of the electric field lines emanating from the edges of the electrodes. Using the complex solution, the field lines are circular arcs where $r_o=(c^2-a^2)/2c$ and $r_i=(b^2-a^2)/2b$. Rotating the circular arcs about the centerline creates a volume that is bounded by two semi-toroidal surfaces representing the measuring volume in cubic centimeters where $R_o=0.5c$ and $R_i=a+0.5(b-a)$. The total capacitance between the ground and driven electrodes can be derived from the complex potential field of a two-dimensional conformal mapping solution as:

$$C = 2a\in \ln[(c^2-a^2)/(b^2-a^2)] = N\in;$$

where $\in$ is the permittivity of the material through which the electric field passes and N is the geometric probe constant.

The selection of the proper geometry for a capacitive sensor such as that shown at FIG. 3 is dependent upon the application. Maximum and minimum penetration depth must be considered as well as the ability to detect changes in permittivity within the measuring volume as a function of capacitance.

When a capacitive sensor such as that shown at FIG. 3 is placed in close proximity to a dielectric material such as a non-metallic or plastic pipe, and if driven electrode 301, guard electrode 303, and ground electrode 302 are at ground voltage, and a DC voltage signal greater than the ground voltage is applied for some period of time to driven electrode 301 and guard electrode 303, the resulting electric field between driven electrode 301 and ground electrode 302 will pass through the dielectric material, and the capacitance of the dielectric material may be determined by a capacitance measurement device.

The capacitance of a given dielectric material is expected to be substantially constant for a completely homogenous material. As a result, anomalies in the material may be localized by determining the capacitance using a capacitive sensor such as that illustrated at FIG. 3 at various locations in close proximity to the material. Because the capacitive sensor at FIG. 3 can only determine the capacitance of the material within the volume of the electric field between driven electrode 301 and ground electrode 303, anomalies may be detected by employing the capacitive sensor at a plurality of locations in close proximity to the material surface. At each location where capacitance measurement occurs, the material within the volume of the electric field is evaluated for homogeneity. A change in the capacitance determined at a location as compared to values determined at other locations may then be utilized to indicate an anomaly in the material within the volume of the electric field at that location. This is illustrated at FIG. 4.

Figure 4:
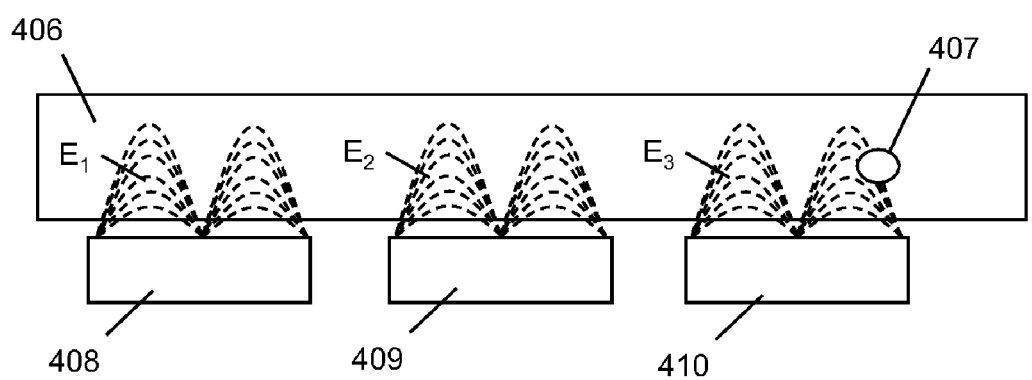
FIG. 4 illustrates an electric field extending through a dielectric material.

FIG. 4 shows non-metallic or plastic material 406 containing anomaly 407. Material 406 is substantially homogenous with the exception of anomaly 407, which may be an air bubble, a material gap, or some other type of anomaly having a capacitance which deviates from material 406. 408 indicates a capacitive sensor at a first location, 409 indicates the same capacitive sensor at a second location, and 410 indicates the same capacitive sensor at a third location. Electric field $E_1$ is generated by the capacitive sensor at the first location, electric field $E_2$ is generated by the capacitive sensor at the second location, and electric field $E_3$ is generated by the capacitive sensor at the third location. $E_1$, $E_2$, and $E_3$ extend through material 406 as shown. As indicated, at the first location and the second location, the volume of material 406 enclosed by electric fields $E_1$ and $E_2$ is substantially homogenous, and the capacitive sensor would be expected to determine substantially equivalent capacitance measurements at the first and second location. At the third location, the volume of material 406 impacted by electric field $E_3$ includes some portion of anomaly 407, which has a capacitance deviating from material 406. As a result, the capacitive sensor would be expected to determine a capacitance at the third location which deviates from the first and second locations. Comparison of the capacitance indicated at the first and second locations with the capacitance indicated at the third location would indicate the presence of anomaly 407 in material 406. Further, the general location of anomaly 407 within material 406 may be determined by correlating the anomalous capacitance reading and the third location.

As is indicated at FIG. 4, the ability of the capacitive sensor to detect anomalies such as anomaly 407 depends on the maximum and minimum penetration depths of the electric field and the resultant measuring volume. The maximum and minimum penetration depths and the resultant measuring volume may be determined from the dimensions of the driven electrode, the guard electrode, and the ground electrode of the capacitive sensor, as is known in the art. The selection of the proper geometry is dependent on the application. Additionally, the capacitive sensor must have sufficient proximity to the dielectric material under inspection so that the resultant measuring volume encounters the locations where anomalies are expected. Within this disclosure, when the capacitive sensor is placed in close proximity to the material under inspection such as material 407, this is meant to indicate that the electric field within the resultant measuring volume passes through the material at least to some degree. Thus, within the disclosure, close proximity may indicate a situation where direct physical contact between the capacitive sensor and the material exists, or a situation where contact between the capacitive sensor and the material is not established, but where the capacitive sensor is sufficiently close such that electric field within the resultant measuring volume passes through the material at least to some degree. When capacitance is determined at a plurality of locations such as indicated at FIG. 4, then the close proximity between the capacitive sensor and the material under evaluation should be substantially constant, so that the electric field passes through the material to a similar extent at each location, and such that the capacitances to be compared reflect a similar interaction between the electric field and the material at each point.

Figure 5:
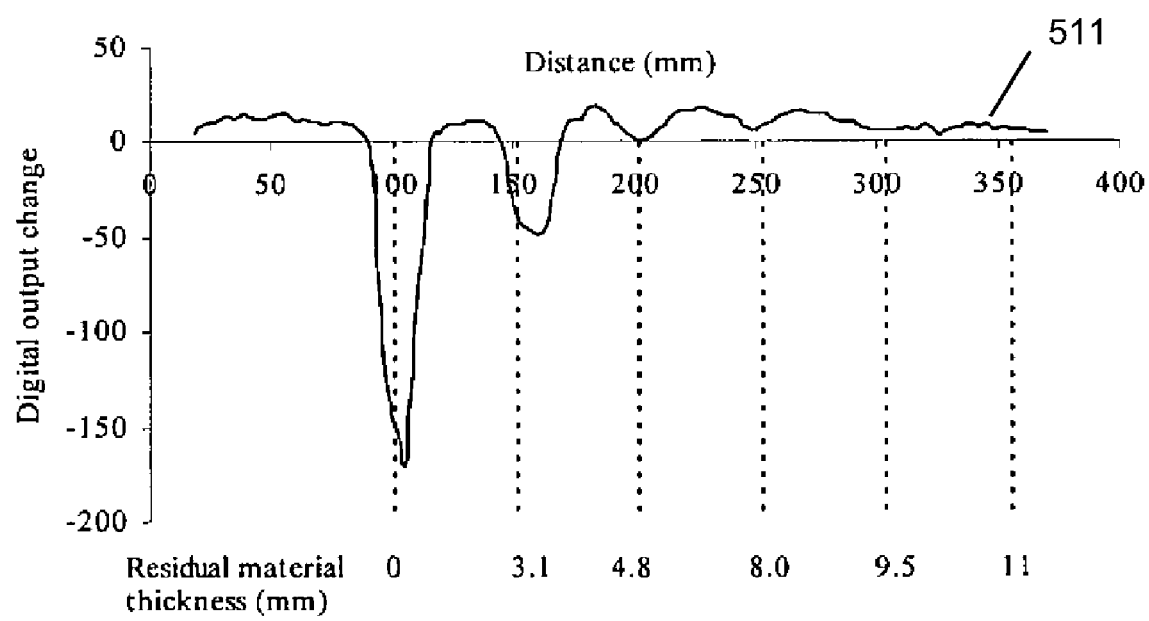
FIG. 5 illustrates an exemplary capacitance-location output.

The principle is demonstrated at FIG. 5. A capacitive sensor similar to that shown at FIG. 3 was constructed where a=7.6 mm, b=9.5 mm, and c=12.7 mm, giving a minimum penetration depth 1.7 mm and a maximum penetration depth of 4.1 mm. A thin layer of acrylic adhesive separated the driven electrode, the guard electrode, and the ground electrode. Six 6.4 mm diameter holes with center to center spacing of 51 mm were drilled from the outside of an acrylic pipe having 14.6 cm inside diameter and 1.25 cm wall thickness. The holes were drilled to various depths from the outside of the pipe so that varying thickness of acrylic separated the bottom of the hole and the inner wall of the acrylic pipe. Hole locations and various residual material remaining between the bottom of the hole and inner wall of the acrylic pipe are indicated at FIG. 5.

The capacitive sensor was connected to a capacitance-to-digital converter and passed through the inside of the acrylic pipe. The capacitance-to-digital converter determined the capacitance of the acrylic pipe material within the measuring volume of the capacitive sensor based on evaluation of the RC time constant of the circuit formed by the driven electrode, the ground electrode, and the capacitance-to-digital converter. The capacitance measurements indicated at 511 were utilized to determine hole location. The capacitive sensor easily detected the holes through 3.1 and 4.8 mm of residual material and marginally through 8.0 mm. Defects through 9.5 mm and 11 mm of residual material were not detected as expected.

The apparatus provided allows determinations such as that depicted at FIG. 5 to detect and locate abnormalities in a dielectric material such as non-metallic or plastic pipe using a capacitive sensor having a driven electrode, a guard electrode, and a ground electrode. The driven electrode and the ground electrode are electrically connected to a capacitance measurement device and form an RC circuit with the capacitance measurement device. The guard electrode is electrically connected to a shield driver to mimic the voltage applied to the driven electrode. The driven electrode, the guard electrode, and the ground electrode are arranged such that when a voltage is supplied to the driven electrode and the guard electrode, a fringing field is established between the driven electrode and the ground electrode. The capacitive sensor is placed in sufficient proximity to the dielectric material so that the electric field extends through the dielectric material. The capacitance measurement device determines a capacitance of the dielectric between the driven electrode and the ground electrode based on the RC time constant of the RC circuit formed, and a capacitance signal from the capacitance measurement device is sent to a processor. The processor is in further data communication with a location device which determines the location of the capacitive sensor with respect to some fixed point, and the processor correlates the capacitance signal and a location signal from the location device, in order to provide output such as that illustrated at FIG. 5. The output provided may be direct reading, or may be stored by the processor and downloaded when the capacitive sensor has completed a sweep over some length of the dielectric material.

Figure 6:
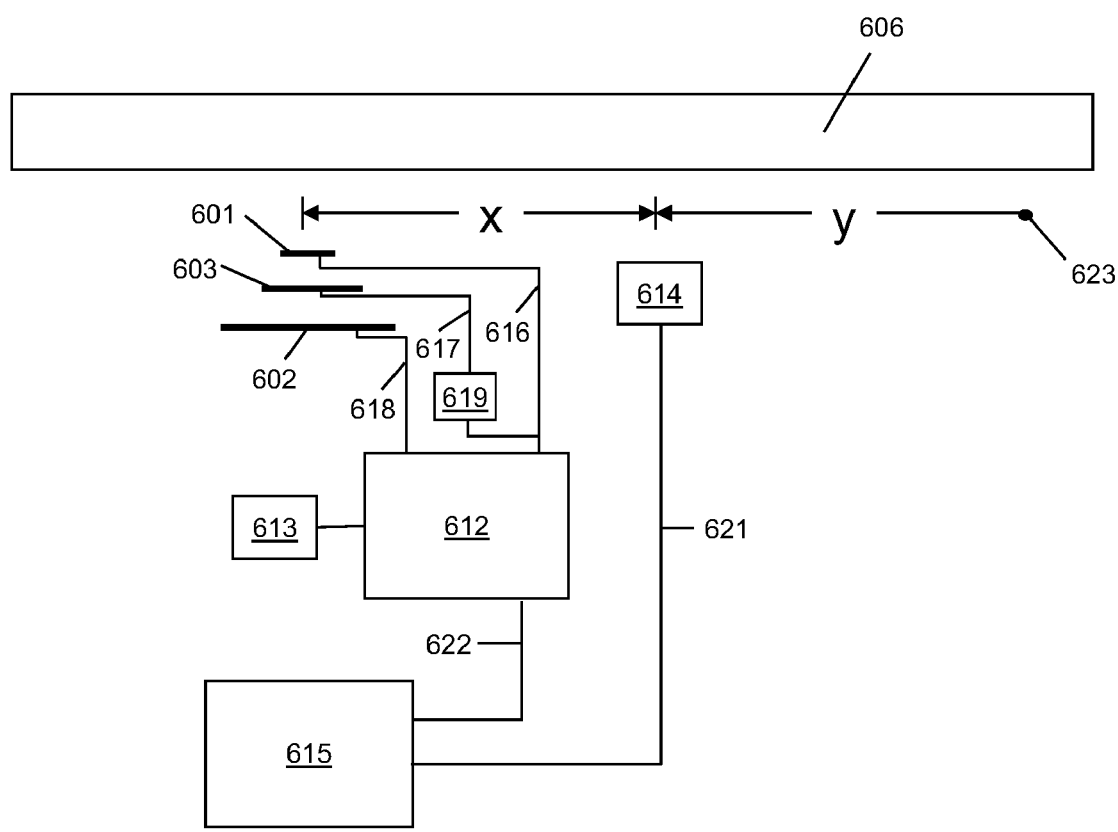
FIG. 6 illustrates a functional schematic of a circuit.

The apparatus is illustrated conceptually at FIG. 6. At FIG. 6, a capacitive sensor is comprised of driven electrode 601, guard electrode 603, and ground electrode 602. Driven electrode 601 and ground electrode 602 are electrically connected to capacitance measurement device 612 through electrical connections 616 and 618 respectively, and form an RC circuit with capacitance measurement device 612. Capacitance measurement device 612 is an analog or digital instrument designed to determine a capacitance between electrodes based on time constant evaluation of an RC circuit formed when electrical connections such as 616 and 618 serve as capacitance measurement device 612 inputs. Power supply 613 provides electrical power for the operation of capacitance measurement device 612 in determining the capacitance of the RC circuit formed by driven electrode 601, ground electrode 602, and capacitance measurement device 612.

Guard electrode 603 is electrically connected to shield driver 619 through electrical connection 617. Shield driver 619 is electrically connected to driven electrode 601, such that shield driver 619 provides an output which mimics the voltage of driven electrode 601, and provides that output to guard electrode 603. Shield driver 619 may be a component separate from capacitance measurement device 612 such as an operational amplifier configured to duplicate the electrical signal provided to driven electrode 601, as is known in the art, or shield driver 619 may be an integral component of capacitance measurement device 612, when capacitance measurement device 612 is an instrument designed to provide an active shield driver output, as is known in the art.

Location device 614 is maintained at a constant position with respect to the capacitive sensor, such that any motion of location device 614 reflects corresponding motion of the capacitive sensor. For example, location device 614 may be some fixed distance X from a fixed point on the capacitive sensor and a variable distance Y to a fixed reference point 623, so that the displacement of the capacitive sensor from the fixed reference point 623 may be determined from the displacement Y between location device 614 and the fixed reference point 623. Location device 614 may be any device capable of sensing device displacement and providing a location signal representative of that displacement. For example, location device 614 may be an optical mouse focused on a surface of material 606, so that sensed movement over the surface may be converted to a displacement.

Capacitance measurement device 612 is in data communication with processor 615 through data connection 622, and location device 614 is in data communication with processor 615 through data connection 621. Processor 615 is programmed to receive a capacitance signal through data connection 622 and a location signal through data connection 621 and correlate the capacitance signal and the location signal.

In operation, the capacitive sensor comprised of driven electrode 601, guard electrode 603, and ground electrode 602 is placed in close proximity to a surface of dielectric material 606 at a first point on the surface of dielectric material 606. Power supply 613 provides electrical power to capacitance measurement device 612, and capacitance measurement device 612 determines a capacitance based on the time constant of the RC circuit formed by capacitance measurement device 612 and the capacitive sensor when driven electrode 601 and guard electrode 603 are energized, and a fringing electric field extends between driven electrode 601 and ground electrode 602. Processor 615 receives a capacitance signal from capacitance measurement device 612 via data connection 622 and receives a location signal from location device 614 via data connection 621. The capacitance signal is representative of the capacitance of the volume of dielectric material 606 within the measuring volume of the fringing electric field between driven electrode 601 and ground electrode 602, and the location signal is representative of the location of the capacitive sensor, by virtue of the constant position of location device 614 with respect to the capacitive sensor. Processor 615 correlates the capacitance signal and the location signal and may provide a direct output or store the values in a data array.

Following measurement at the first point, the capacitive sensor comprised of driven electrode 601, guard electrode 603, and ground electrode 603, and location device 614 may be displaced to a second point and the process may be repeated, to record capacitance and location data for the second point. This may be repeated for any number of points on the surface of dielectric material 606. In an embodiment, processor 615 is in continuous data communication with location device 614, and processor 615 directs capacitance measurement device 612 to take a capacitance measurement when a predetermined displacement since the previous measuring location has occurred, based on data received from location device 614. The processor correlates the capacitance and location data and provides direct output or provides an indication of capacitance versus location such as that depicted at FIG. 5 once all measurements are completed. Anomalies in dielectric 606 are detected based on capacitance measurements obtained as a location as compared to capacitances measured at surrounding locations.

The capacitive sensor comprised of driven electrode 601, guard electrode 603, and ground electrode 602 may be connected to an inspection vehicle through a sensor arm fixably attached to the capacitive sensor and the inspection vehicle. The inspection vehicle may be capable of travel over a length of dielectric material 606, and the sensor arm may be capable of maintaining the capacitive sensor in close proximity to dielectric material 606 over the length of travel. For example, the sensor arm may be a telescoping arm which maintains contact between the capacitive sensor and the dielectric material 606 as the inspection vehicle travels over the length of dielectric material 606. Location device 614 may be similarly fixably attached to the inspection vehicle, so that vehicle inspection travel displaces location device 614 from the fixed point of reference 623, and correspondingly displaces the capacitive sensor.

In operation, the inspection vehicle may be capable of travel through the interior of a non-metallic or plastic pipe. The inspection vehicle may traverse a piping length as the sensor arm maintains the capacitive sensor in close proximity to the inner wall of the piping length. During the traverse of the piping length, the inspection vehicle may travel intermittently such that the inspection vehicle is at rest when capacitive measurements are taken, or the inspection vehicle may move at a constant velocity such that capacitive measurements are taken concurrently with inspection vehicle motion. In the latter case, the accuracy of the capacitance measurement is related to further displacement of the inspection vehicle that occurs over the time elapsed while the capacitance measurement is taken. However, in a typical situation, capacitance measurement will occur over a sufficiently short time period, and inspection vehicle speed will be insufficient to generate a displacement that significantly impacts either the capacitance measurement or the location data correlated by processor 615.

Figure 7A:
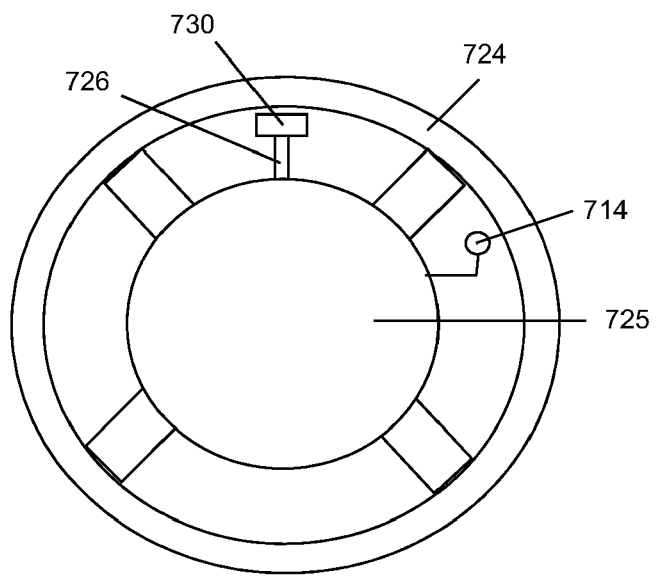
FIG. 7A illustrates a capacitive sensor and inspection vehicle arrangement.

An example of a capacitive sensor and a location device on an inspection vehicle is illustrated at FIG. 7A. Capacitive sensor 730 is comprised of a driven electrode (not shown), a guard electrode (not shown), and a ground electrode (not shown), and is fixably attached to sensor arm 726. Sensor arm 726 is fixably attached to inspection vehicle 725. Location device 714 is also fixably attached to inspection vehicle 725. Inspection vehicle 725 is within the interior of pipe 724, and sensor arm 726 maintains capacitive sensor 730 in close proximity to the inner wall of pipe 724. Inspection vehicle 725 may travel through the interior of pipe 724 in a direction parallel to the longitudinal axis of pipe 724 (either into or out of the page). As inspection vehicle 725 travels though the interior of pipe 724, a processor (not shown) may direct a capacitive measurement device (not shown) to determine capacitance using capacitive sensor 730 at a plurality of points along the inner wall of pipe 724, and provide a capacitance signal at each measurement point to the processor. Similarly, location device 714 provides a location signal to the processor as inspection vehicle 725 transits, so that the processor may correlate location and capacitance data at each measurement point. Anomolies may be detected over the piping length using correlated capacitance measurement and location data, such as that shown at FIG. 5.

FIG. 7A illustrates inspection vehicle 725 utilizing the single capacitive sensor 730. As discussed earlier, as inspection vehicle 725 traverses the interior of pipe 724 and output such as that shown at FIG. 5 is generated, capacitance measurement only occurs within the measurement volume of capacitive sensor 730. The measurement volume of capacitive sensor 730 will typically be significantly less than the volume of material comprising pipe 724 and surrounding inspection vehicle 725. As a result, the output from a single capacitive sensor such as capacitive sensor 730 may only reflect data from a small percentage of the material comprising pipe 724. This may be mitigated by using a plurality of capacitive sensors fixably attached to inspection vehicle 725, as is shown as FIG. 7B. At FIG. 7B, capacitive sensors 730 through 733 are each comprised of a driven electrode (not shown), a guard electrode (not shown), and a ground electrode (not shown), and are fixably attached to sensor arms 726 through 729 respectively. Sensor arms 726 through 729 are fixably attached to inspection vehicle 725, and location device 714 is fixably attached to inspection vehicle 725. As inspection vehicle 725 traverses the interior of pipe 724, capacitance measurements may be taken with each of the capacitive sensors 730-733, increasing the aggregate measurement volume so that a greater percentage of material comprising pipe 730 is evaluated. Any number of capacitive sensors may be utilized in this manner to increase the circumferential coverage of the plurality of capacitive sensors as an inspection vehicle transits through the interior of a piping section. A sufficient number of capacitive sensors arranged in a manner similar to that shown at FIG. 7B may provide substantially complete circumferential coverage as the inspection vehicle transits through the interior of the pipe.

Figure 7B:
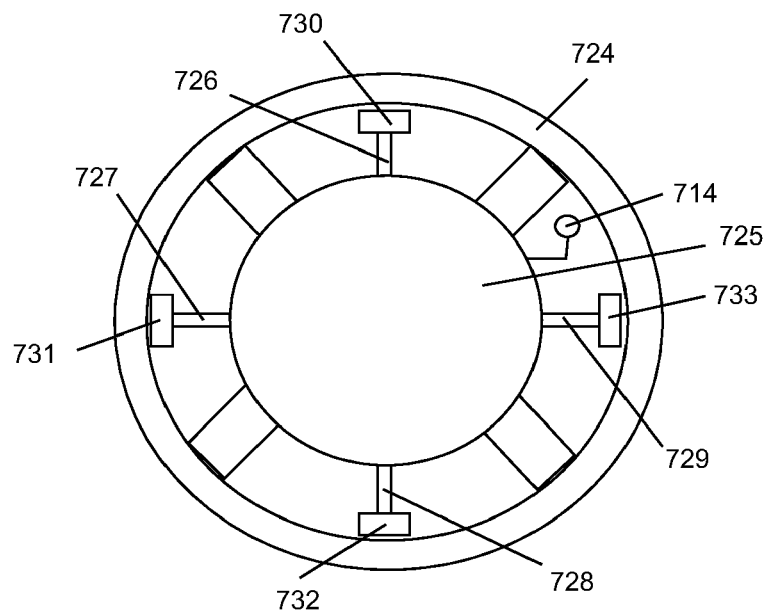
FIG. 7B illustrates a second capacitive sensor and inspection vehicle arrangement.

When a plurality of capacitive sensors such as shown at FIG. 7B are utilized, each capacitive sensor in the plurality of capacitive sensors is electrically connected to a single capacitance measurement device, so that a plurality of capacitance measurement devices is similarly required. In an embodiment, the capacitance measurement device electrically connected to the each capacitive sensor is an integrated circuit chip fixably attached to the each capacitive sensor. Such an arrangement allows capacitance measurement to occur close to the capacitive sensor, so that noise, circuit resistivity, stray capacitances, and other potential environmental impacts on the measurement may be mitigated.

When a plurality of capacitive sensors and a corresponding plurality of capacitance measurement devices are utilized, a single capacitance measurement device in the plurality of capacitance measurement devices may be electrically connected to a power supply serving only that single capacitance measurement device, or the single capacitance measurement device may be connected to a central power supply serving multiple capacitance measurement devices. Similarly, a single capacitance measurement device may be in data communication with a processor serving only that single capacitance measurement device, or the single capacitance measurement device may be in data communication with a central processor serving all capacitance measurement devices. Location data for each capacitive sensor in the plurality of capacitive sensors may be provided by location device 714 based on the known spatial orientation of each capacitive sensor with respect to location device 714.

Sensors arms 726 through 729 may be telescoping arms powered by a spring, a motor, hydraulics, or other means known in the art, so that the capacitive sensors fixably attached are maintained in close proximity to the inner wall of pipe 724 as inspection vehicle 725 traverses the piping length.

Further, inspection vehicle 725 may also carry the power supply and the processor as on-board payloads to mitigate the necessity of cables extending from the inspection vehicle to support equipment outside the pipe inspection environment.

An advantage of this disclosure is the determination of capacitance using a capacitive measurement device based on time constant determination. This greatly mitigates the impact of environmental noise on the sensitivity of the capacitive sensor as the voltage level is reduced, as opposed to methods which utilize an AC signal in order to determine an impedance using phase shift and signal loss parameters. As a result, the required power supply may be significantly less complex. Further, the reduced voltages allowed by the time-domain determination of capacitance within this disclosure provides significant advantage when operating in certain environments where the allowed voltage level may be limited because of, for example, an explosive hazard or other safety factors. This provides a significant flexibility in operation.

DESCRIPTION OF AN EMBODIMENT

Figure 8:
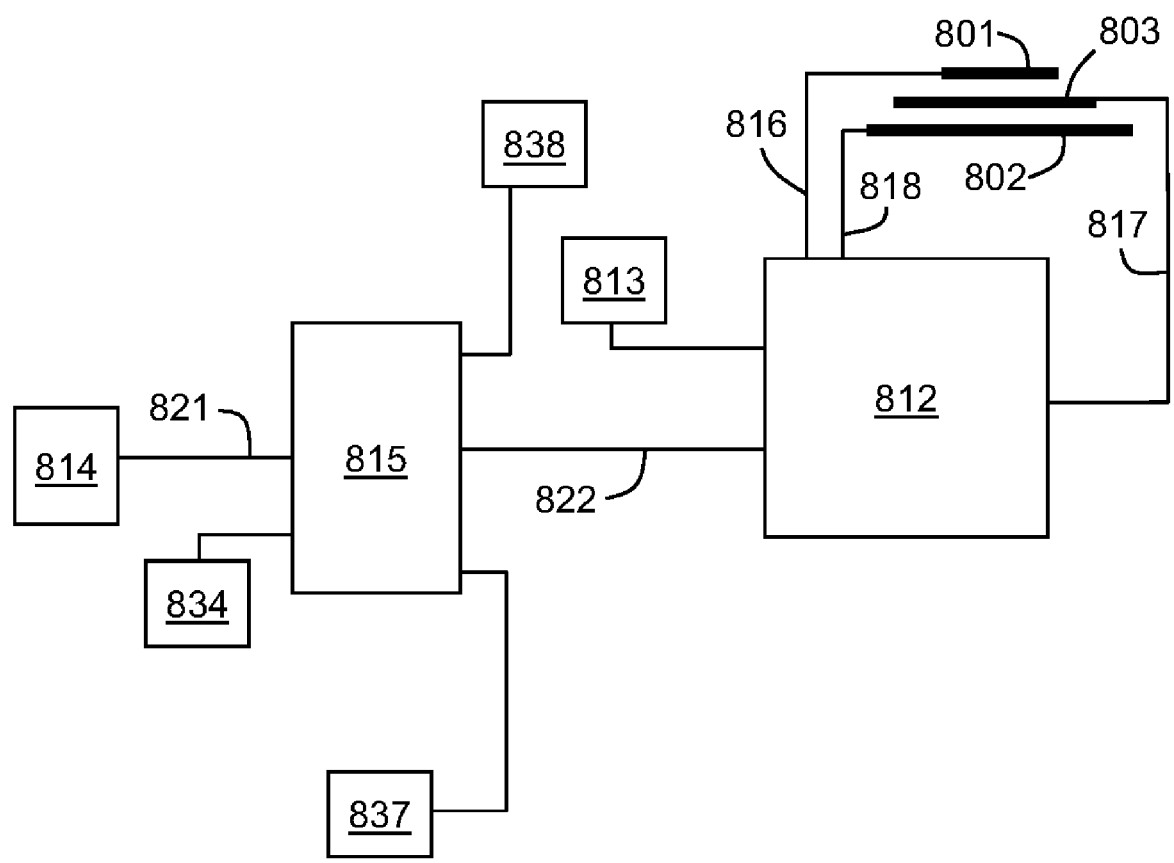
FIG. 8 illustrates a specific embodiment of the apparatus.

An embodiment which may be carried onboard an inspection vehicle such as inspection vehicle 725 is illustrated schematically at FIG. 8. FIG. 8 illustrates a capacitive sensor comprised of driven electrode 801, guard electrode 803, and ground electrode 802. Driven electrode 801 and ground electrode 802 are electrically connected to capacitance measurement device 812 through electrical connections 816 and 818 respectively. In the embodiment shown, capacitance measurement device 812 is a capacitance-to digital integrated chip designed to determine a capacitance between electrodes based on time constant evaluation of an RC circuit formed when electrical connections such as 816 and 818 serve as capacitance measurement device 812 inputs. Additionally, guard electrode 803 is electrically connected to a shield driver (not shown). In the embodiment shown, the shield driver (not shown) is integral to the capacitance-to-digital integrated chip functioning as capacitance measurement device 812. Capacitance measurement device 812 is in data communication with processor 815 through data connection 822 and is electrically connected to power supply 813.

In an embodiment, capacitance measurement device 812 is an ANALOG DEVICES AD7747 24-bit Capacitance to Digital Converter capable of high precision capacitance measurements with resolution down to 40 aF, and using a $I^2C$ serial communication format for communication with processor 815 through data connection 822. The chip provides an active shield driver output that is used in the capacitive sensor and provides a built in temperature sensing element which may be read to provide temperature data taken physically at the chip.

In the embodiment shown, power supply 813 is a DC battery electrically connected to a voltage regulator, and supplies a constant DC voltage to capacitance measurement device 812. In a particular embodiment, power supply 813 is a nickel metal hydride 9 volt battery electrically connected to an LM317 voltage regulator, and provides 5.0 volts until battery voltage drops to about 6.5 volts. In another embodiment, a 12 volt lead acid gel cell serves as the battery. Power supply 813 may also provide power to other components illustrated at FIG. 8, or the other components may utilize a power supply separate from power supply 813.

In the embodiment shown, processor 815 is a programmable microcontroller. In a particular embodiment, processor 815 is a MICROCHIP PIC16F877A microcontroller with built-in RAM, ROM, I/O, microprocessor, timers and counters. The chip may be programmed in circuit by using ICSP connector 838. In this embodiment, processor 815 is further in data communication with master clock 834, a 20 MHz quartz crystal, which provides timing for capacitance measurement device 812 and location device 814 through processor 815.

In the embodiment shown, location device 814 is an optical location chip providing a location signal to processor 815 through data connection 821. In a particular embodiment, location device 814 is an AGILENT ADNS-2610 optical mouse encoder utilizing an LED illuminated micro camera to measure movement with a resolution of 400 counts per inch. Location data for the capacitive sensor is determined based on the sensed motion of the inner wall of the piping section as the inspection vehicle travels through the piping section, and the resulting signal is sent from location device 814 to processor 815. The chip counts motion starting at zero and resets each time it is read via a serial connection to processor 815. The processor 815 maintains a cumulative value from read to read in order to measure distances between measurements as well as overall position.

Processor 815 coordinates the timing of capacitance measurements generated by capacitance measurement device 812 and location data provided by location device 814 using a timing device such as master clock 834. When processor 815 determines that a predetermined displacement since the last measured point has occurred based on the location signal from location device 814, processor 815 directs capacitance measurement device 812 to conduct capacitance measurement utilizing the capacitive sensor comprised of driven electrode 801, guard electrode 803, and ground electrode 802. In response, capacitance measurement device 812 energizes driven electrode 801 and guard electrode 803, and a fringing electric field between driven electrode 801 and ground electrode 802 is established. Capacitance measurement device 812 determines a capacitance between driven electrode 801 and ground electrode 802 and sends a capacitance signal to processor 815.

In the embodiment shown, processor 815 correlates the capacitance signal and the location signal and provides the capacitance and location data to output device 837. In a particular embodiment, output device 837 is a microwave serial link module and a MAX232 RS-232 buffer chip providing communication to a host PC for data collection and display, so that wireless communication allows autonomous operation of the probe with no tether to bind or disturb the motion of the probe while traversing a pipe length. Output device 837 may also store the capacitance and location data onboard, so that the data may be retrieved from output device 837 following inspection of the pipe length.

The components illustrated at FIG. 8 may be hosted on a microcontroller board and carried as payload on an inspection vehicle such as inspection vehicle 725. In an embodiment, the microcontroller board is an OLIMEX 40 pin PIC microcontroller project board. When a plurality of capacitive sensors such as shown at FIG. 7B is utilized, each capacitive sensor in the plurality of capacitive sensors is electrically connected to a single capacitance measurement device such as capacitance measurement device 812. Power supply 813, processor 815, and location device 814 may similarly serve a single capacitive sensor, or may serve multiple capacitive sensors in the plurality of capacitive sensors.

When the components illustrated at FIG. 8 are carried as payload in an inspection vehicle such as inspection vehicle 725, the inspection vehicle may be any type of vehicle that can be modified to carry the payloads associated with this disclose within the environment under which the piping inspection occurs. Motive force for the inspection vehicle may be supplied in any suitable manner, for example, the inspection vehicle may includes drive mechanisms such as wheels, crawlers, wall press, walking, inchworm, screw and pushrods. For example, vehicles disclosed in U.S. Pat. No. 6,427,602 to Hovis et al., issued Aug. 6, 2002; U.S. Pat. No. 4,986,314 to Himmler, issued Jan. 22, 1991; U.S. Pat. No. 5,878,783 to Smart, issued Mar. 9, 1999, among others, are suitable for use when modified to carry the payloads provided in this disclosure.

In operation, when an inspection vehicle such as inspection vehicle 725 is utilized, a sensor arm such as a spring loaded telescoping suspension holds the capacitive sensor in close proximity to the inner wall of the pipe under test, such that the capacitive sensor may retract if a weld seam or physical pipe discontinuity is traversed during the inspection vehicle's traverse through the piping interior. During the traverse, processor 815 may tally the location data provided by location device 814 and when a predetermined displacement has occurred since the last measurement, processor 815 may signal capacitance measurement device 812 to initiate a capacitance measurement. Processor 815 then reads the capacitance signal from capacitance measurement device 812 and sends it to output device 837 along with location data from location device 814, and processor 815 begins the loop over again waiting for the proper distance increment to take and transmit another capacitance and location reading.

As discussed previously, within this disclosure, when a capacitive sensor such as capacitive sensor 703 is placed in close proximity to the material under inspection such as material comprising pipe 724, this is meant to indicate that the electric field within the resultant measuring volume passes through the material at least to some degree. However, as is understood in the art, an air gap between the capacitive sensor and the material under inspection would be expected to reduce the sensitivity of the resulting measurement. As a result, in one embodiment, sensors arms such as sensor arms 726 through 730 establish physical contact between the capacitive sensors and the inner wall of pipe 724, so that any air gap and the resulting impact on measurement is substantially mitigated. In this embodiment, the driven electrode, the guard electrode, and the ground electrode comprising the capacitive sensor may be comprised of rigid material conformed to the inner curvature of the pipe under inspection. Alternatively, the driven electrode, the guard electrode, and the ground electrode comprising the capacitive sensor may be made of a flexible material, so that contact established between the capacitive sensor and the inner wall of a pipe acts to conform the capacitive sensor to the inner curvature. The flexible capacitive sensor may be fabricated in multi-layer flexible circuit board material. The flexible capacitive sensor is thin and durable and may be affixed to sensor arms using adhesives. The flexible capacitive sensor may be fabricated using photographic techniques creating precise electrode geometries, uniformity, and interchangeability.

Figure 9:
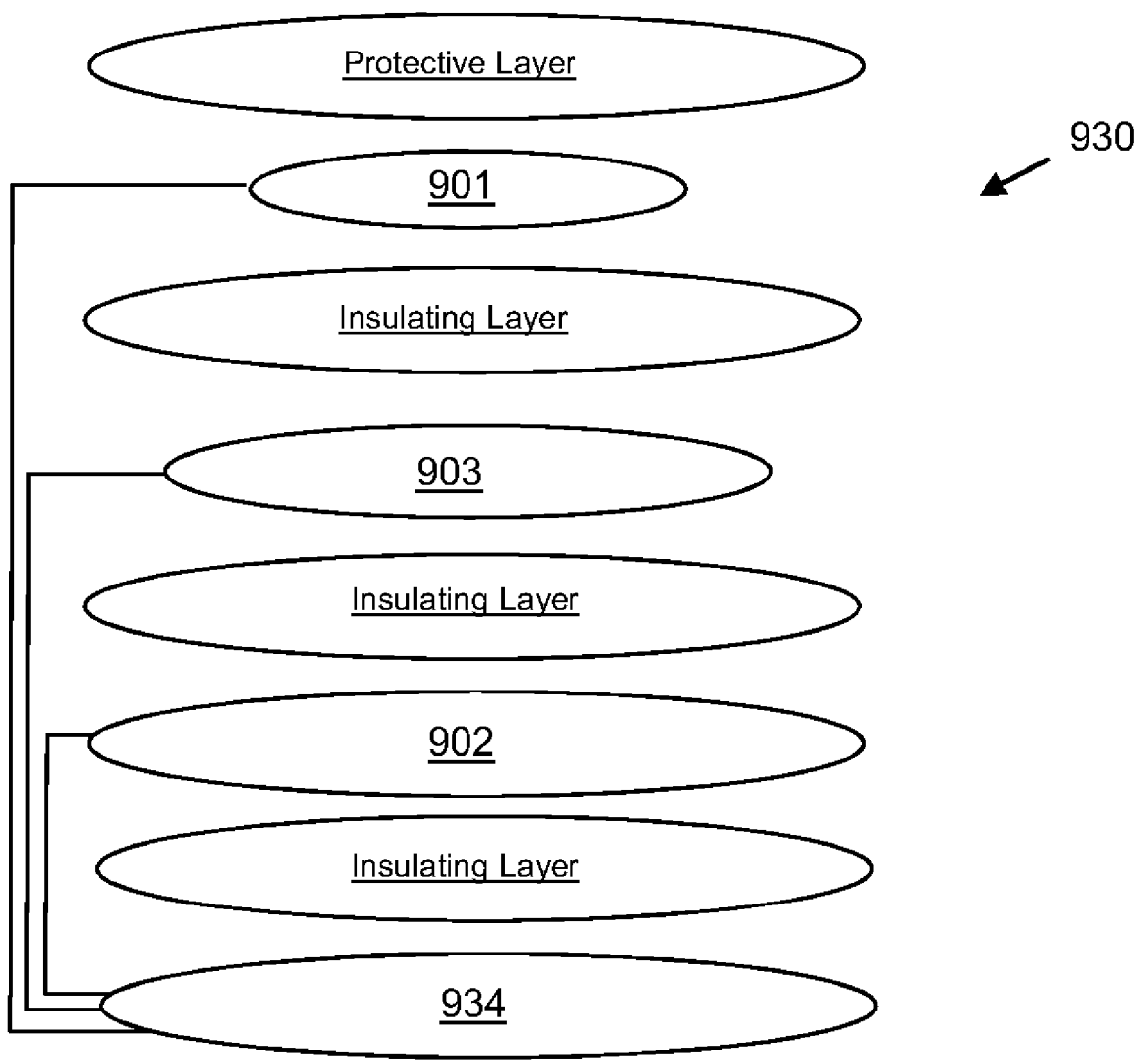
FIG. 9 illustrates a specific embodiment of a capacitive sensor.

FIG. 9 illustrates an embodiment of a flexible capacitive sensor generally indicated at 930. Driven electrode 901 is a first disc, guard electrode 903 is a second disk, and ground electrode 902 is a third disk, where the diameter of the first disk is less than or equal to the diameter of the second disk, and where the diameter of the second disk is less than the diameter of the third disc, and where the center of the first disk, the second disk, and the third disk are collinear. In a particular embodiment, driven electrode 901, guard electrode 903, and ground electrode 902 are comprised of copper disks etched using a photolithographic technique. The protective layer and the insulating layers between the driven electrode 901, guard electrode 903, and ground electrode 902 are layers of flexible insulating material, such as KAPTON. The protective layer, the electrode layers, and the insulating layers may be compressed and bonded in an oven using high temperature adhesive, as is understood in the art. Control surface 934 may contain circuit traces and integrated circuits for the necessary electrical and data connections serving driven electrode 901, guard electrode 903, and ground electrode 902.

In another embodiment similar to that shown at FIG. 9, the driven electrode is a first disc, the guard electrode is a second disk, and the ground electrode is an annulus, and where the center of the first disk, the second disk, and the annulus are collinear. Removing the center of the ground electrode to form an annulus reduces the inherent built-in capacitance while not impacting the projected electric field. As a result, the capacitive sensor charges more quickly and requires less power to charge. In a specific configuration of this embodiment, the diameter of the first disk is less than or equal to the diameter of the second disk, and the diameter of the second disk is less than the outer diameter of the annulus but larger than the inner diameter of the annulus.

Exemplary Results

An embodiment similar to that depicted at FIGS. 7 and 8 was utilized to detect twelve defects of various sizes placed in a 4 m length of 0.15 m diameter, 12.7 mm wall thickness, polyethylene pipe. The locations and characteristics of the defects are indicated at Table 1. All defects were located at the same circumferential position. Defect depth ranged from 6.4 to 19.1 mm with volumes between 0.28 to 0.72 cc.

Figure 10:
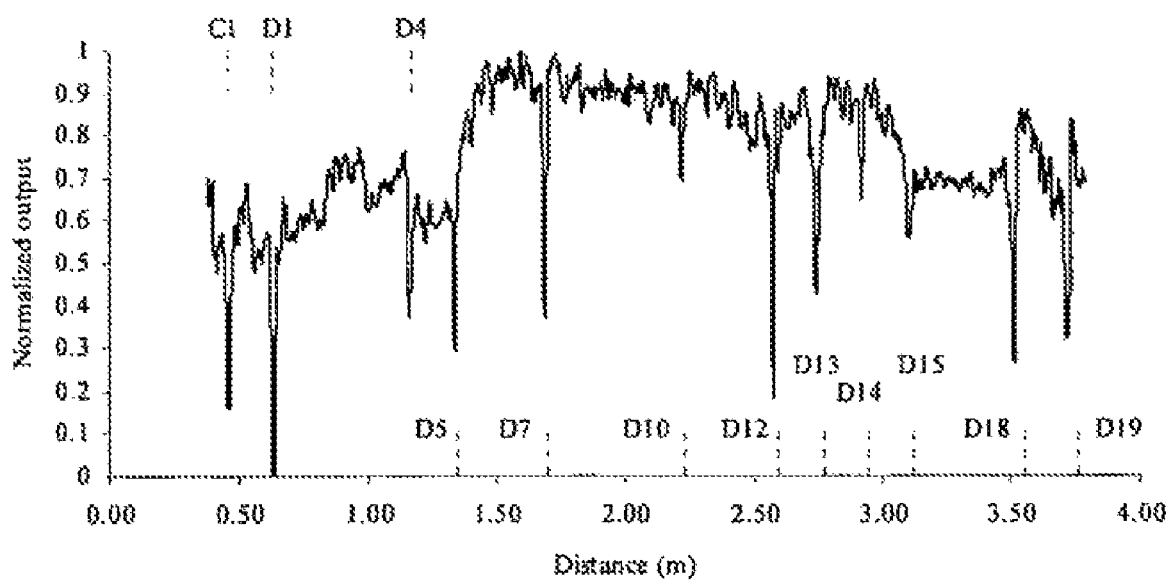
FIG. 10 illustrates an exemplary capacitance-location output of a specific embodiment.

FIG. 10 is a representative example of a scan. The results of FIG. 10 were produced by transiting the inspection vehicle through the interior of the pipe and programming the processor such that a capacitance measurement was taken and correlated every $1/10^{th}$ of an inch. The position of each defect corresponding to Table 1 was accurately located using the apparatus of this disclosure.

A probe has been designed and tested that can detect defects existing on the outer wall of polyethylene pipe or non-metallic pipe from the interior wall. The probe may be self powered thus allowing the device to be placed in existing underground pipe and allowed to accumulate data concerning pipe integrity and then retrieved later for analysis.

Having described the basic concept of the invention, it will be apparent to those skilled in the art that the foregoing detailed disclosure is intended to be presented by way of example only, and is not limiting. Various alterations, improvements, and modifications are intended to be suggested and are within the scope and spirit of the present invention. Additionally, the recited order of elements or sequences, or the use of numbers, letters, or other designations therefore, is not intended to limit the claimed processes to any order except as may be specified in the claims. Accordingly, the invention is limited only by the following claims and equivalents thereto.

All publications and patent documents cited in this application are incorporated by reference in their entirety for all purposes to the same extent as if each individual publication or patent document were so individually denoted.

TABLE 1

Characteristics of defects in polyethylene pipe

| Defect # | Location | Volume | Depth | Diameter | Comments |
|---|---|---|---|---|---|
| C1 | 0.457 | 0.46 | 6.4 | 9.5 | Round defect |
| D1 | 0.635 | 0.72 | 10.2 | 9.5 | Round defect |
| D2 | — | — | — | — | No defect in region |
| D3 | — | — | — | — | No defect in region |
| D4 | 1.168 | 0.36 | 11.4 | 6.4 | Round defect |
| D5 | 1.346 | 0.41 | 5.1 | 3.2 | Saw cut 25.4 mm long, 3.2 mm wide |
| D6 | — | — | — | — | No defect in region |
| D7 | 1.702 | 0.72 | 10.2 | 9.5 | Round defect |
| D8 | — | — | — | — | No defect in region |
| D9 | — | — | — | — | No defect in region |
| D10 | 2.235 | 0.28 | 8.9 | 6.4 | Round defect |
| D11 | — | — | — | — | No defect in region |
| D12 | 2.591 | 0.66 | 8.9 | 3.2 | Saw cut 22.9 mm long, 3.2 mm wide |
| D13 | 2.769 | 0.66 | 2.3 | 19.1 | Round defect |
| D14 | 2.946 | 0.25 | 3.6 | 9.5 | Round defect |
| D15 | 3.124 3.137 | 0.28 ea. | 8.9 ea. | 6.4 ea. | 2 identical holes 12.7 mm apart |
| D16 | — | — | — | — | No defect in region |
| D17 | — | — | — | — | No defect in region |
| D18 | 3.556 | 0.57 | 2.0 | 19.1 | Round defect |
| D19 | 3.759 | 0.51 | 1.8 | 19.1 | Round defect |

We claim:

1. An apparatus for the inspection of a length of a dielectric material using a capacitive sensor comprising:

the capacitive sensor, where the capacitive sensor is comprised of a driven electrode, a ground electrode, and a guard electrode, where the guard electrode is between the driven electrode and the ground electrode such that a position vector from a first point on the driven capacitor to a second point on the ground capacitor crosses or intersects the guard capacitor, such that when a constant voltage not equal to a voltage of the ground electrode is supplied to the driven electrode and the guard electrode, a fringing electric field is established between at least the driven electrode and the ground electrode;

a capacitance measurement device, the capacitance measurement device electrically connected to the driven electrode, and the capacitance measurement device electrically connected to the ground electrode, such that the capacitance measurement device forms an RC circuit with the driven electrode and the ground electrode and such that the capacitance measurement device may determine a capacitance between the driven electrode and the ground electrode based on a time constant of the RC circuit, and the capacitance measurement device in data communication with a processor;

a shield driver electrically connected to the driven electrode and electrically connected to the guard electrode, such that the shield driver senses a voltage supplied to the driven electrode and provides an equivalent voltage to the guard electrode;

a power supply electrically connected to the capacitance measurement device;

a location device maintained at a fixed distance from the capacitive sensor, and the location device in data communication with the processor; and the processor, the processor programmed to receive a location signal via data communication with the location device, where the location signal is representative of a location of the location device, and the processor programmed to receive a capacitance signal from the capacitance measurement device, where the capacitance signal is representative of the capacitance between the driven electrode and the ground electrode, and the processor programmed to correlate the capacitance signal and the location signal to provide an output indicating the capacitance signal and the location signal.

2. The apparatus of claim 1 where the processor is programmed to direct the capacitance measurement device to determine the capacitance between the driven electrode and the ground electrode when the location of the location device achieves a predetermined value.

3. The apparatus of claim 1 further comprising an inspection vehicle, the inspection vehicle able to travel over a surface of the dielectric material, and the inspection vehicle having a sensor arm and the capacitive sensor fixably attached to the sensor arm, where the sensor arm places the capacitive sensor in close proximity to the surface of the dielectric material when the inspection vehicle travels on the surface of the dielectric material, and the power supply, the capacitance measurement device, and the location device attached to the inspection vehicle.

4. The apparatus of claim 1 where the dielectric material is a dielectric piping material comprising a pipe, and where the surface of the dielectric material is an inner wall of the pipe.

5. The apparatus of claim 1 where the capacitance measurement device is an integrated circuit chip fixably attached to the capacitive sensor, and where the capacitance signal is a digital signal.

6. The apparatus of claim 3 where the capacitance measurement device is an integrated circuit chip fixably attached to the capacitive sensor, and where the location device is a digital signal processor in data communication with an imaging system, where the imaging system is positioned such that when the inspection vehicle travels over the surface of the dielectric material, the imaging system generates images of the surface of the dielectric material, and where the processor is a programmable microcontroller, and where the processor is fixably attached to the inspection vehicle.

7. The apparatus of claim 3 where the capacitive sensor and the capacitance measurement device form a capacitance measurement package, and where the inspection vehicle has a plurality of sensor arms, and where a plurality of capacitance measurement packages are fixably attached to the inspection vehicle such that each sensor arm in the plurality of sensor arms is fixably attached to one capacitive sensor in the plurality of capacitance measurement packages.

8. The apparatus of claim 1 where the driven electrode, the guard electrode, and the ground electrode are comprised of a flexible material, such that when the capacitive sensor is placed in contact with a surface of the dielectric material, the capacitive sensor substantially conforms to the surface of the dielectric material.

9. The apparatus of claim 1 where the driven electrode is a first disc, the guard electrode is a second disc, and the ground electrode is a third disc, and where the driven electrode, the guard electrode, and the ground electrode are arranged such that the center of the first disc, the center of the second disc, and the center of the third disc are collinear, and where a diameter of the first disk is less than or equal to a diameter of the second disk, and where a diameter of the third disk is greater than the diameter of the second disk.

10. The apparatus of claim 1 where the driven electrode is a first disc, the guard electrode is a second disk, and the ground electrode is an annulus, and where the driven electrode, the guard electrode, and the ground electrode are arranged such that the center of the first disc, the center of the second annulus, and the center of the annulus are collinear, and where a diameter of the first disk is less than or equal to a diameter of the second disk, and where an outer diameter of the annulus is greater than the diameter of the second disk.

11. A method of dielectric material inspection using the apparatus of claim 1 comprising:

placing the capacitive sensor in close proximity to a surface of the dielectric material at a first location on the surface of the dielectric material while the driven electrode and the guard electrode have substantially equivalent voltage to the ground electrode;

supplying a voltage signal to the driven electrode using the capacitance measurement device powered by the power supply, thereby increasing the voltage of the driven electrode and the guard electrode;

determining the capacitance between the driven electrode and the ground electrode using the capacitance measurement device while the voltage signal to the driven electrode is supplied, and transmitting the capacitance signal to the processor using the capacitance measurement device;

transmitting the location signal from the location device to the processor, where the location signal is representative of the first location; and observing a capacitance-location data point indicated by the processor, where the capacitance-location data point is comprised of the capacitance indicated by the processor and the location indicated by the processor.

12. The method of claim 11 further comprising:

recording the capacitance-location data point;

selecting a plurality of measurement points, where a measurement point is a point on the surface of the dielectric material, and for each measurement point in the plurality of measurement points, repeating the placing the capacitive sensor in close proximity to the surface of the dielectric material step, the supplying a voltage signal to the driven electrode step, the determining the capacitance between the driven electrode and the ground electrode step, the transmitting the location signal from the location device to the processor step, the observing the capacitance-location data point step, and the recording the capacitance-location data point step using the each measurement point as the first location, thereby generating a plurality of capacitance-location data points; and analyzing the plurality of capacitance-location data points and identifying specific capacitance-location data points in the plurality of capacitance-location data points which indicate a capacitance value falling outside of an expected range.

13. The method of claim 12 where the dielectric material is a dielectric piping material comprising a pipe, and where the surface of the dielectric material is an inner wall of the pipe, and where the plurality of measurement points lie substantially on a line parallel to a longitudinal axis of the pipe, and including displacing the capacitive sensor progressively further from the first location in a direction parallel to the longitudinal axis of the pipe, such that the repeating the placing the capacitive sensor in close proximity to the surface of the dielectric material step, the supplying a voltage signal to the driven electrode step, the determining the capacitance between the driven electrode and the ground electrode step, the transmitting the location signal from the location device to the processor step, the observing the capacitance-location data point step, and the recording the capacitance-location data point step for the each measurement point is conducted as the capacitive sensor is displaced progressively further from the first location in a direction parallel to the longitudinal axis of the pipe.

14. The method of claim 13 where displacing the capacitive sensor progressively further from the first location in a direction parallel to the longitudinal axis of the pipe occurs at a constant velocity, such that the plurality of capacitance-location points is generated as the capacitive sensor is displaced at the constant velocity.

15. An apparatus for the inspection of a piping length, where the piping length is comprised of a dielectric piping material and where the piping length has a longitudinal axis, comprising:
 a plurality of capacitance measurement packages, where each capacitance measurement package is comprised of,
 a capacitive sensor, where the capacitive sensor is comprised of a driven electrode, a ground electrode, and a guard electrode, where the guard electrode is between the driven electrode and the ground electrode such that a position vector from a first point on the driven capacitor to a second point on the ground capacitor crosses or intersects the guard capacitor, such that when a constant voltage not equal to a voltage of the ground electrode is supplied to the driven electrode and the guard electrode, a fringing electric field is established between at least the driven electrode and the ground electrode, and
 a capacitance measurement device, the capacitance measurement device electrically connected to the driven electrode, and the capacitance measurement device electrically connected to the ground electrode, such that the capacitance measurement device forms an RC circuit with the driven electrode and the ground electrode and such that the capacitance measurement device may determine a capacitance between the driven electrode and the ground electrode based on a time constant of the RC circuit, and the capacitance measurement device electrically connected to a power supply and the capacitance measurement device in data communication with a processor;
 a shield driver electrically connected to the driven electrode and electrically connected to the guard electrode, such that the shield driver senses a voltage supplied to the driven electrode and provides an equivalent voltage to the guard electrode;
 an inspection vehicle capable of traveling through an interior of the piping length over the longitudinal axis of the piping length, the inspection vehicle comprised of,
 a chassis,
 a plurality of sensor arms equal in quantity to the plurality of capacitance measurement packages and extending from the chassis, where each sensor arm in the plurality of sensor arms is fixably attached to a single capacitance measurement package in the plurality of capacitance measurement packages and the single capacitance measurement package is fixably attached to only the each sensor arm, and where the each sensor arm places the capacitive sensor comprising the single capacitance measurement package in close proximity to an inner wall of the piping length when the inspection vehicle travels through the interior of the piping length,
 the power supply fixably attached to the chassis and,
 a location device fixably attached to the chassis, and the location device in data communication with the processor; and
 the processor, the processor programmed to receive a location signal via data communication with the location device, where the location signal is representative of a location of the location device, and the processor programmed to receive a capacitance signal from each capacitance measurement package in the plurality of capacitance measurement packages, where the capacitance signal is representative of the capacitance between the driven electrode and the ground electrode of each capacitance measurement package in the plurality of capacitance measurement packages, and the processor programmed to correlate the capacitance signal from each capacitance measurement package in the plurality of capacitance measurement packages and the location signal to provide an output indicating the capacitance signal from each capacitance measurement package in the plurality of capacitance measurement packages capacitance signal and the location signal.

16. The apparatus of claim 15 where placing the capacitive sensor comprising the single capacitance measurement package in close proximity to the inner wall of the piping length places the capacitive sensor comprising the single capacitance measurement package in contact with the inner wall of the piping length, and where the driven electrodes, the guard electrodes, and the ground electrodes comprising the plurality of capacitive sensors are comprised of a flexible material, such that the driven electrodes, the guard electrodes, and the ground electrodes comprising the plurality of capacitive sensors substantially conform to the curvature of the inner wall of the piping length.

17. The apparatus of claim 16 where the capacitance measurement device comprising each capacitance measurement package in the plurality of capacitance measurement packages is an integrated circuit chip fixably attached to the capacitive sensor comprising the each capacitance measurement package in the plurality of capacitance measurement packages, and where the capacitance signal from the each capacitance measurement package in the plurality of capacitance measurement packages is a digital signal.

18. The apparatus of claim 17 where the processor is a plurality of programmable microcontrollers equal in quantity to the plurality of capacitance measurement packages, and where each programmable microcontroller in the plurality of programmable microcontrollers is in data communication with one capacitance measurement package in the plurality of capacitance measurement packages and the one capacitance measurement package is in data communication with only the each programmable microcontroller in the plurality of programmable microcontrollers, and where the each programmable microcontroller in the plurality of programmable microcontrollers is in data communication with the location device, and where the each programmable microcontroller in the plurality of programmable microcontrollers is programmed to direct the one capacitance measurement package to determine a measured capacitance when the location of the location device achieves a predetermined value.

19. The apparatus of claim 17 where the single capacitive sensor in the plurality of capacitive sensors is comprised of a first disc, a second disc, and a third disc, and where the first disc is the driven electrode for the single capacitive sensor in the plurality of capacitive sensors, the second disc is the guard electrode for the single capacitive sensor in the plurality of capacitive sensors, and the third disc is the ground electrode for the single capacitive sensor in the plurality of capacitive sensors, and where the first disc, the second disc, and the third disc are arranged such that the center of the first disc, the center of the second disc, and the center of the third disc are collinear, and where a diameter of the first disk is less than or equal to a diameter of the second disk, and where a diameter of the third disk is greater than the diameter of the second disk.

20. The apparatus of claim 17 where the single capacitive sensor in the plurality of capacitive sensors is comprised of a first disc, a second disc, and an annulus, and where the first disc is the driven electrode for the single capacitive sensor in the plurality of capacitive sensors, the second disc is the guard electrode for the single capacitive sensor in the plurality of capacitive sensors, and the annulus is the ground electrode for the single capacitive sensor in the plurality of capacitive sensors, and where the first disc, the second disc, and the annulus are arranged such that the center of the first disc, the center of the second disc, and the center of the annulus are collinear, and where a diameter of the first disk is less than or equal to a diameter of the second disk, and where an outer diameter of the annulus is greater than the diameter of the second disk.

* * * * *